(12) United States Patent
Mazur et al.

(10) Patent No.: US 7,864,312 B2
(45) Date of Patent: Jan. 4, 2011

(54) SUBSTRATES FOR RAMAN SPECTROSCOPY HAVING DISCONTINUOUS METAL COATINGS

(75) Inventors: Eric Mazur, Concord, MA (US); Eric Diebold, Boston, MA (US)

(73) Assignee: President and Fellows of Harvard College, Cambridge, MA (US)

(*) Notice: Subject to any disclaimer, the term of this patent is extended or adjusted under 35 U.S.C. 154(b) by 241 days.

(21) Appl. No.: 12/017,698

(22) Filed: Jan. 22, 2008

(65) Prior Publication Data

US 2009/0033929 A1 Feb. 5, 2009

Related U.S. Application Data

(60) Provisional application No. 60/962,538, filed on Jul. 30, 2007.

(51) Int. Cl.
*G01J 3/44* (2006.01)

(52) U.S. Cl. .................................................. 356/301

(58) Field of Classification Search ........................ None
See application file for complete search history.

(56) References Cited

U.S. PATENT DOCUMENTS

| | | | |
|---|---|---|---|
| 4,965,430 A | 10/1990 | Curtis et al. | |
| 5,534,068 A | 7/1996 | Beach et al. | |
| 5,538,674 A | 7/1996 | Nisper et al. | |
| 5,557,409 A | 9/1996 | Downer et al. | |
| 6,350,397 B1 * | 2/2002 | Heikkila et al. | 264/39 |
| 6,376,177 B1 | 4/2002 | Poponin | |
| 6,406,777 B1 | 6/2002 | Boss et al. | |
| 7,057,256 B2 | 6/2006 | Carey, III et al. | |
| 7,354,792 B2 | 4/2008 | Carey, III et al. | |
| 7,586,601 B2 | 9/2009 | Ebstein | |
| 2002/0149769 A1 | 10/2002 | Roorda et al. | |
| 2003/0029495 A1 | 2/2003 | Mazur et al. | |
| 2003/0059820 A1 | 3/2003 | Vo-Dinh | |
| 2003/0213715 A1 | 11/2003 | Klepac et al. | |
| 2004/0101469 A1 | 5/2004 | Demers | |
| 2004/0150818 A1 | 8/2004 | Armstrong et al. | |
| 2004/0162554 A1 | 8/2004 | Lee et al. | |

(Continued)

FOREIGN PATENT DOCUMENTS

DE 202004008333 8/2004

(Continued)

OTHER PUBLICATIONS

Keller S, et al., "Quality control of food with near-infrared-excited Raman spectroscopy" Fresenius Journal of Analytical Chemistry, vol. 346, Jun. 1993, pp. 863-867.

(Continued)

*Primary Examiner*—Tu T Nguyen
(74) *Attorney, Agent, or Firm*—Thomas J. Engellenner; Reza Mollaaghababa; Nutter McClennen & Fish LLP

(57) ABSTRACT

In one aspect, the present invention provides methods for fabricating substrates for use in a variety of analytical and/or diagnostic applications. Such a substrate can be generated by exposing a semiconductor surface (e.g., silicon surface) to a plurality of short laser pulses to generate micron-sized, and preferably submicron-sized, structures on the surface. The structured surface can then be coated with discontinuous metal coating characterized by one or more metalized surface region and a plurality of surface gaps.

22 Claims, 10 Drawing Sheets

U.S. PATENT DOCUMENTS

| | | | |
|---|---|---|---|
| 2004/0163758 | A1 | 8/2004 | Kagan et al. |
| 2005/0112544 | A1 | 5/2005 | Xu et al. |
| 2006/0038990 | A1 | 2/2006 | Habib et al. |
| 2006/0079062 | A1 | 4/2006 | Mazur et al. |
| 2006/0158653 | A1 | 7/2006 | Chiarello et al. |
| 2006/0209413 | A1 | 9/2006 | Kim et al. |
| 2006/0246573 | A1 | 11/2006 | Kurane et al. |
| 2007/0115469 | A1 | 5/2007 | Ebstein |
| 2007/0247620 | A1* | 10/2007 | Koo .......................... 356/301 |
| 2009/0033929 | A1 | 2/2009 | Mazur et al. |
| 2009/0279085 | A1 | 11/2009 | Ebstein |

FOREIGN PATENT DOCUMENTS

| | | |
|---|---|---|
| EP | 1382459 | 1/2004 |
| EP | 1416325 | 5/2004 |
| EP | 1731962 | 12/2006 |
| WO | WO-02077608 | 10/2002 |
| WO | WO-2006060734 | 6/2006 |
| WO | WO-2006086014 | 8/2006 |
| WO | WO-2006138442 | 12/2006 |
| WO | WO-2007060989 | 5/2007 |
| WO | WO-2008091852 | 7/2008 |
| WO | WO-2008091858 | 7/2008 |

OTHER PUBLICATIONS

Montoya, et al., "Detection of *Salmonella* using Surfaced Enhanced Raman Scattering" Chemical and Biological Sensing IV, Proceedings of SPIE, vol. 5085, Apr. 21, 2003, pp. 144-152.

Liu, et al., "Nanowell surface enhanced Raman scattering arrays fabricated by soft-lithography for label-free biomolecular detections in integrated microfluidics," 2005 American Institute of Physics, Applied Physics Letters 87 (3 pages).

Stuart, et al., "Biological applications of localised surface plasmonic phenomenae", 20050201; 20050200, vol. 152, No. 1, pp. 13-32, XP006023676.

Jung, et al., "Facile fabrication of large area nanostructures for efficient surface-enhanced Raman scattering," J. Mater. Chem., 2006, 16, 3145-3149.

Kneipp, et al., "Population Pumping of Excited Vibrational States by Spontaneous Surface-Enhanced Raman Scattering," The American Physical Society, Physical Review Letters, vol. 76, No. 14, Apr. 1, 1996, pp. 2444-2447.

Ihlemann, J. et al., "Excimer Laser Micro Machining of Inorganic Dielectrics" Applied Surface Science, Elsevier, Amsterdam, NL, vol. 106, Oct. 1, 1996, pp. 282-286, XP000879307 ISSN: 0169-4332.

Xia, Q. et al., "Ultrafest Patterning of Nanostructures in Polymers Using Laser Assisted Nanoimprint Lithography" Applied Physics Letters, AIP, American Institute of Physics, Melville, NY, vol. 83, No. 21, Nov. 24, 2003, pp. 4417-4419, XP001191757, ISSN: 003-6951.

Vo-Dinh, Surface-Ehanced Rama Spectrometry With Silver Particles on Stochasitc-Post Substrates, Analytica Chimica Acta, 1986, 139-148, vol. 181.

Vo-Dinh et al., Plasmonics-Based Nanostructures for Surface-Enhanced Raman Scattering Bioanalysis, Methods in Molecular Biology, 2005, 255-283, vol. 300.

Henley et al., Excimer laser nanostructuring of nickel thin films for the catalytic growth of carbon nanotubes, Applied Physics Letters, 2004, 4035, 84.

Henley et al., Laser-Nanostructured Ag Films as Substrates for Surface-Enhanced Raman Spectroscopy, Applied Physics Letters, 2006, 081904, 88.

Lehmann, et al., Fabrication of submicron crossed square wave gratings by dry etching and thermoplastic replication techniques, Journal of Vacuum Science Technology, Oct.-Dec. 1983, pp. 1207-1210, vol. 1, No. 4.

Nie et al., Probing Single Molecules and Single Nanoparticles by Surface-Enhanced Raman Scattering, Science Feb. 21, 1997, pp. 1102-1106, vol. 275.

Campion, et al., Surface-enhanced Raman scattering, Chemical Society Reviews, 1998, pp. 241-250, vol. 27.

Kneipp, et al., Ultrasenstive Chemical Analysis by Raman Spectroscopy, Chemical Review, 1999, pp. 2957-2975, vol. 99.

Emory, et al., Direct Observation of Size-Dependent Optical Enhancement in Single Metal Nanoparticles, Journal of American Chemical Society, 1998, pp. 8009-8010, vol. 120.

Kottmann, et al., Plasmon resonant coupling in metallic nanowires, Optics Express, Jun. 4, 2001, pp. 655-663, vol. 8, issue 12.

Jiang, et al., Single Molecule Raman Spectroscopy at the Junctions of Large Ag Nanocrystals, Journal of Physical Chemistry, 2003, pp. 9964-9972, vol. 107.

Genov, et al., Resonant Field Enhancements from Metal Nanoparticle Arrays, Nano Letters, 2004, pp. 153-158, vol. 4, issue 1.

Cao, et al., Nanoparticles with Raman Spectroscopic Fingerprints for DNA and RNA Detection, Science, Aug. 30, 2002, pp. 1536-1340, vol. 297.

Liu, et al., Nanopillar Substrates for SERS, Proceedings of the 7th International Conf. on Miniaturized Chemical and Biochemical Analysis Systems, Oct. 5-9, 2003, pp. 705-708.

Liu, et al., Cinfigurable 3D Nanoscale High Aspect Ratio Pillars for Surface-Enhanced Raman Spectroscopy IEEE 2003, pp. 425-427.

Liu et al., Nanowell surface enhanced Raman scattering arrays fabricated by soft-lithography for label-free biomolecular detections in integrated microfluidics, Applied Physics Letters, 2005, pp. 074101-1-074101-3, vol. 87.

Duyne, et al., Atomic force microscopy and surface-enhanced Raman spectroscopy I. Ag island films and Ag film over polymer nanosphere surfaces supported on glass, Journal of Chemical Physics, Aug. 1, 1993, pp. 2101-2115, vol. 99, issue 3.

Quagliano, The SERS Effect as a Tool for Studying Molecules Absorbed on Semiconductor Surfaces, The Internet Journal of Vibrational Spectroscopy, 2004, vol. 4, Edition 2.

Drachev, et al., Adaptive silver films towards bio-array applications, Proc. of SPIE vol. 5703.

Haynes, et al., Nanosphere Lithography: A Versatile Nanofabrication Tool for Studies of Size-Dependent Nanoparticle Optics, Journal of Physical Chemistry, 2001, pp. 5599-5611, vol. 105, Issue 24.

Zhang, et al., An electrochemical surface-enhanced Raman spectroscopy approach to anthrax detection, Proc. of SPIE, vol. 5221, pp. 82-91.

Drachev, et al., Adaptive Silver Films for Detection of Antibody-Antigen Binding, 2005, pp. 8368-8373, vol. 21, Issue 18.

Lyandres, et al., Real-Time Glucose Sensing by Surface-Enhanced Raman Spectroscopy in Bovine Plasma Facilitated by a Mixed Decanethiol/Mercaptohexanol Partition Layer, Analytical Chemistry, Oct. 1, 2005, pp. 6134-6139, vol. 77, Issue 19.

Fagano, et al., Raman Spectroscopic Study of the Avidin-Biotin Complex, Journal of Raman Spectroscopy, 1995, pp. 991-995, vol. 26.

Duyne, et al., Spatially Resolved Surface Enhanced Raman Spectroscopy: Feasibility, Intensity Dependence on Sampling Area and Attomole Mass Sensitivity, May 2, 1986, pp. 190-196, vol. 126, issue 2.

Drachev, et al, Surface-Enhanced Raman Difference between Human Insulin and Insulin Lispro Detected with Adaptive Nanostructures, Journal of Physical Chemistry, 2004, pp. 18046-18052, vol. 108.

Kneipp, et al., Single Molecule Detection Using Surface-Enhanced Raman Scattering (SERS), Physical Review Letters, Mar. 3, 1997, pp. 1667-1670, vol. 78, issue 9.

Haynes, et al., Plasmon Scanned Surface-Enhanced Raman Scattering Excitation Profiles, Materials Research Society Symposia Proceedings, 2002, p. 7.1-7.6, vol. 728.

Her, et al., Femtosecond laser-induced formation of spikes on silicon, Applied Physicals A. Materials Science & Processing, 2000, pp. 383-385, vol. 70.

Shen, et al., Femtosecond laser-induced formation of submicrometer spikes on silicon in water, Applied Physicals Letters, Dec. 6, 2004, pp. 5694-5696, vol. 85, issue 23.

Shen, et al., Formation of regular arrays of siliconmicrospikes by femtosecond laser irradiation through a mask, Applied Physics Letters, pp. 1715-1717, vol. 82, issue 11.

Laibinis, et al., Comparison of the Structures and Wetting Properties of Self-Assembled Monolayers of n-Alkanethiols on the Coinage Metal Surfaces, Cu, Ag, Au, Journal of the American Chemical Society, 1991, pp. 7152-7167, vol. 113.

Sockalingum, et al., Raman and SERS spectroscopy for probing drug-target interactions: from in-vitro models to intracellular imaging, Internet Journal of Vibrational Spectroscopy.

Astilean, et al., Ordered Metallic Nanostructures for Surface-Enhanced Raman Spectroscopy, Romanian Reports in Physics, 2004, pp. 346-351, vol. 56, issue 3.

Bergman, et al., Relationship between surface-enhanced Raman scattering and the dielectric properties of aggregared silver films, Optics Letters, Jan. 1981, pp. 33-35, vol. 6, issue 1.

Katayama, et al., Formation of ring patterns surrounded by ripples by single-shot laser irradiation with ultrashort pulse width at the solid/liquid interface, Applied Physics Letters, Jun. 16, 2003, pp. 4244-4246, vol. 82, No. 24.

Sylvia, et al., Surface-Enhanced Raman Detection of 2,4-Dinitrotoleune Impurity Vapor as a Marker to Locate Landmines, Analytical Chemistry, Dec. 1, 2000, pp. 5834, 5840, vol. 72.

Quagilano, et al., The SERS Effect as a Tool for Studying Molecules Adsorbed on Semiconductor Surfaces, The Internet Journal of Vibrational Spectroscopy, vol. 4, Ed. 2 (2004).

Office Action dated Mar. 23, 2009 for U.S. Appl. No. 12/017,720.

International Search Report and Written Opinion dated Aug. 14, 2008 for PCT/US2008/051643.

International Search Report and Written Opinion dated Aug. 14, 2008 for PCT/US2008/051647.

Ru, et al., "Surface Enhanced Raman Scattering Enhancement Factors: A Comprehensive Study," J. Phys. Chem. C. 2007, 111, 13794-13803.

Ebstein, S., "Protest Under 37 CRF 1.291", dated Feb. 18, 2009.

Lehmann, et al., "Fabrication of submicron crossed square wave gratings by dry etching and thermoplastic replication techniques," J. Vac.Sci. Technol. B 1(4), pp. 1207-1210.

Duyne, et al., "Atomic force microscopy and surface-enhanced Raman spectroscopy. I. Ag island films and Ag film over polymer nanosphere surfaces supported on glass," J. Chem. Phys. 99(3), pp. 2101-2115 (1993).

* cited by examiner

STOKES 1 SEC

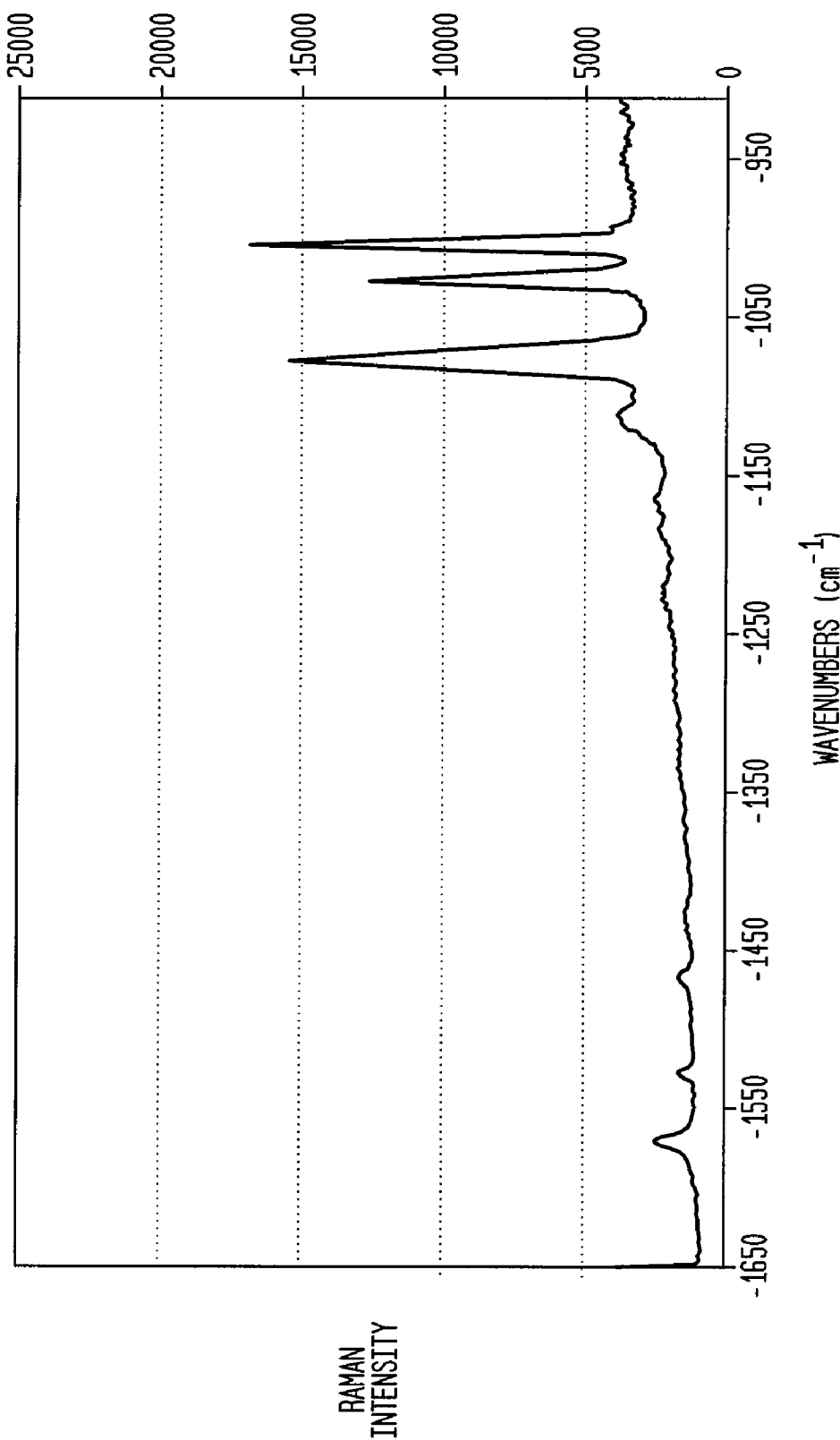

SUBSTRATES FOR RAMAN SPECTROSCOPY HAVING DISCONTINUOUS METAL COATINGS

RELATED APPLICATION

The present application claims priority to a provisional application entitled "Metalized Semiconductor Substrates for Raman Spectroscopy," filed on Jul. 30, 2007 and having a Ser. No. 60/962,538.

BACKGROUND

The present invention relates generally to methods for fabricating substrates suitable for use in analytical and diagnostic optical methods and systems, and in particular, substrates for use in Raman spectroscopy.

Raman spectroscopy can be employed as an analytical as well as a diagnostic technique in a variety of applications, such as material characterization and identification. It relies on inelastic scattering of incident photons by a molecule, via coupling to its vibrational modes, to provide an essentially unique signature for that molecule. In particular, such inelastic scattering (commonly known as Raman scattering) can cause a decrease or an increase in the scattered photon energy, which appear as "Stokes" and "anti-Stokes" peaks in a wavelength-dispersed spectrum of the scattered photons. A drawback of Raman spectroscopy is the relatively few incidences of such inelastic scattering. The probability that a scattering event will occur is typically called "cross-section," which is expressed in terms of area.

Raman scattering cross-sections can, however, be significantly enhanced by placing the molecule on or near a conductive surface. Such a mode of performing Raman spectroscopy is commonly known as surface enhanced Raman spectroscopy (SERS). Although SERS is a promising technique for extending the use of Raman spectroscopy to a variety of new applications, its use is currently limited due to a dearth of reliable, high performance substrates.

Accordingly, there is a need for substrates for use in SERS, as well as other applications, that can provide a high degree of reliability and performance. There is also a need for methods of fabricating such substrates with a high degree of reproducibility, which can be easily and, preferably inexpensively, implemented.

SUMMARY

In one aspect, the present invention provides methods for fabricating sensing substrates suitable for use in a variety of applications, such as Raman spectroscopy, which include generating micron-sized and/or submicron-sized features (e.g., protruding cone-like structures) on a substrate surface (e.g., a semiconductor substrate such as silicon) and forming a discontinuous metal coating characterized by a plurality of gaps (unmetalized regions) on the structured surface. The metalized surface can be employed in a variety of analytical and diagnostic applications, such as Raman spectroscopy.

In a related aspect, the method includes generating micron-sized, and preferably submicron-sized structures, on a semiconductor surface, e.g., a silicon surface, by exposing the surface to a plurality of short laser pulses, e.g., sub-picosecond pulses (e.g., pulses having durations in a range of about 100 femtoseconds ($10^{-15}$ seconds) to about one picosecond ($10^{-12}$ seconds)). In many cases, the pulses are applied to the surface while the surface is in contact with a liquid, e.g., polar or a non-polar liquid. Subsequently, the structured semiconductor surface is metalized so as to form a discontinuous metal coating characterized by a plurality of gaps on the structured surface. In many cases, one or more metalized regions of the coating are formed by a plurality of metal particles, preferably having a maximum dimension less than about 1 micron, or less than about 500 nm, or less than about 100 nm, or less than about 50 nm, while the surface gaps that are distributed, e.g., randomly, throughout the coating correspond to those surface regions that are substantially devoid of such metal particles.

In a related aspect, a method of fabricating a sensing substrate is disclosed, which includes exposing a semiconductor surface to a plurality of short laser pulses to generate a plurality of micron-sized and/or submicron-sized structures therein. One or more metalized coating regions are formed on the structured surface such that a plurality of unmetalized surface regions (that is, gaps in the metal coating) remain present on that surface. In many embodiments, a plurality of metal particles, e.g., having sizes in a range of about 10 to about 500 nm, and more typically in a range of about 50 nm to about 100 nm, form the metalized region(s).

In another aspect, a diagnostic method is disclosed that includes generating a plurality of micron-sized and/or submicron-sized structures on a substrate surface, e.g., a semiconductor surface, by exposing the surface to a plurality of short laser pulses, followed by disposing a quantity of metal onto the structured surface so as to generate a discontinuous metal coating characterized by a plurality of surface gaps distributed throughout the coating. The metalized structured surface can then be utilized for a diagnostic assay, e.g., for performing Raman spectroscopy.

In other aspect, a sensing substrate, e.g., a substrate suitable for use in Raman spectroscopy, and other analytical and/or diagnostic applications, is disclosed that includes a semiconductor substrate, e.g., a silicon wafer, having a surface that exhibits micron-sized, and/or preferably submicron-sized, structures. A metalized coating is disposed on that structured surface, where the coating includes one or more metalized regions and a plurality of unmetalized gaps. In a related aspect, the metalized regions are formed by a plurality of metal particles, e.g., metal particles having sizes less than about 1 micron.

Further understanding of the invention can be obtained by reference to the following detailed description in conjunction with the associated drawings, which are briefly described below.

BRIEF DESCRIPTION OF THE DRAWINGS

FIG. 11B presents the anti-Stokes peaks of the 1572 cm$^{-1}$ band of a BTh SAM deposited on a silver coated structured silicon surface in accordance with one embodiment of the invention obtained with a 100 second integration.

DETAILED DESCRIPTION

The present invention generally provides sensing substrates that are suitable for use in a variety of applications, including surface enhanced Raman spectroscopy (SERS). In some embodiments, a surface of a semiconductor substrate, e.g., silicon, is exposed to a plurality of short laser pulses (e.g., sub-picosecond laser pulses) to generate micron-sized, and preferably submicron-sized, structures (e.g., in the form of spikes) on that surface. A plurality of metalized coating regions can then be formed on the structured surface (e.g., by evaporating a metal onto the substrate) such that a plurality of surface gaps (i.e., unmetalized regions) are also present on the structured surface. Such a surface can be utilized in a variety of sensing applications, such as SERS, as discussed in more detail below. The terms "structured surface" or "rough surface" are used herein interchangeably to refer to a surface that exhibits undulations (e.g., spikes) with peak-to-trough excursions (e.g., amplitudes) of a few microns (e.g., less than about 20 microns), and preferably less than about 1 micron, and more preferably less than about 100 nanometers (e.g., in a range of about 1 nm to about 50 nm). The "structured surface" can exhibit a surface roughness with amplitudes less than about 1 micron, and preferably less than about 100 nanometers, and more preferably less than about 50 nm. Further, although in the embodiments that follow various aspects of the invention are discussed by reference to semiconductor substrates, in other embodiments, other types of substrates, such as glass or metallic substrates or other materials suitable for structuring (e.g., micro- or nanostructuring), can be utilized.

Figure 1:
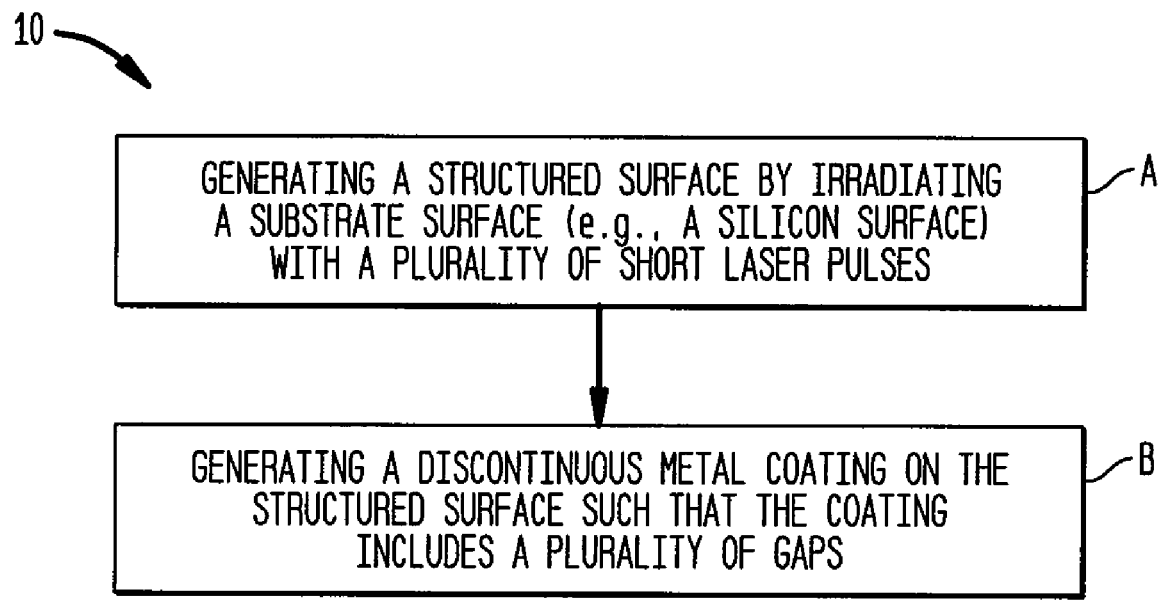
FIG. 1 is a flow chart depicting various steps in some exemplary embodiments of methods of the invention for generating a metalized semiconductor sensing substrate, FIG. 2 schematically depicts an exemplary apparatus suitable for generating micron-sized or submicron-sized structures on a substrate's surface, such as a semiconductor surface.

With reference to a flow chart 10 shown in FIG. 1, an exemplary method in accordance with one embodiment of the invention for fabricating a sensing substrate such as a semiconductor sensing substrate, e.g., one suitable for use in surface enhanced Raman spectroscopy (SERS), comprises generating a structured surface (step A) by irradiating a substrate surface (e.g., a semiconductor surface, such as a silicon surface) with a plurality of short laser pulses. The term "short laser pulses," as used herein, refers to laser pulses having durations less than about a few nanoseconds ($10^{-9}$ seconds), e.g., pulses with durations in a range of about 100 femtoseconds ($10^{-15}$ seconds) to about one picosecond ($10^{-12}$ seconds). By way of example, in some embodiments, a silicon substrate can be exposed to a plurality of short pulses (e.g., pulses having durations in a range of about 100 femtoseconds to about 500 femtoseconds) while the surface is in contact with a fluid, e.g., water. The pulses cause a change in surface topography characterized by surface undulations (e.g., surface roughness) having amplitudes less than about a few microns (e.g., less than about 10 microns), and preferably less than about 1 micron, e.g., in a range of about 50 nm to about 200 nanometers.

Figure 2:
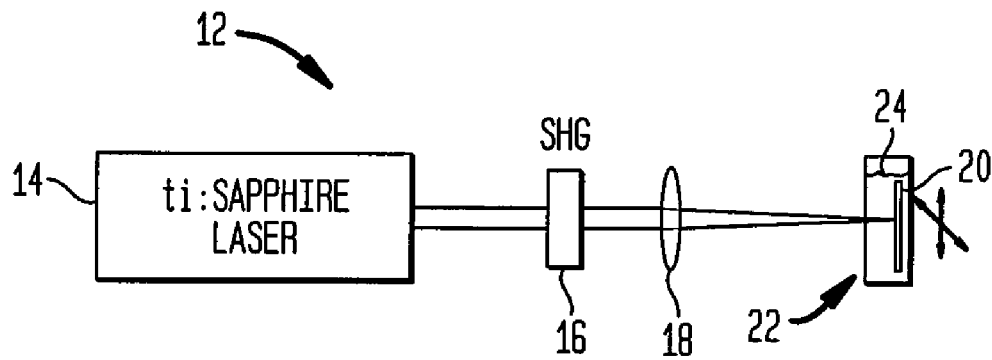

By way of example, FIG. 2 schematically depicts an exemplary optical system 12 suitable for processing a substrate (e.g., a semiconductor substrate) so as to generate micron-sized, and preferably submicron-sized, features (structures) on a surface thereof. For example, the features can include a plurality of spikes, e.g., substantially columnar structures extending from the surface to a height above the surface. The optical system 12 includes a Titanium-Sapphire (Ti:Sapphire) laser 14 for generating short laser pulses. By way of example, the Ti:Sapphire laser can generate laser pulses with a pulse width of about 80 femtoseconds at 800 nm wavelength (e.g., at an average power of 300 mW and at a repetition rate of 95 MHz). The pulses generated by the Ti:Sapphire laser can be applied to a chirped-pulse regenerative amplifier (not shown) that, in turn, can produce, e.g., 0.4 millijoule (mJ)), 100 femtosecond pulses at a wavelength of 800 nm and at a repetition rate of about 1 kilohertz.

The optical system 12 further includes a harmonic generation system 16 that receives the amplified pulses and doubles their frequency to produce, e.g., 100-femtosecond second-harmonic pulses at a wavelength of 400 nanometers. A lens 18 focuses the second-harmonic pulses onto a surface of a semiconductor sample 20, which can be disposed on a three-dimensional translation system (not shown). A glass liquid cell 22 can be coupled to the semiconductor sample so as to allow the sample surface exposed to the pulses to have contact with a liquid 24 (e.g., water) contained within the cell. Further details regarding methods and apparatuses for generating micron-sized, and preferably submicron-sized, features on a semiconductor surface can be found in co-pending U.S. patent application entitled "Femtosecond Laser-Induced Formation Of Submicrometer Spikes On A Semiconductor Substrate" having a Ser. No. 11/196,929, filed Aug. 4, 2005, which is herein incorporated by reference. U.S. Pat. No. 7,057,256 entitled "Silicon-Based Visible And Near-Infrared Optoelectronic Devices" and Published U.S. Patent Application No. 2003/00299495 entitled "Systems And Methods For Light Absorption and Field Emission Using Microstructured Silicon," both of which are herein incorporated by reference, provide further disclosures regarding microstructuring silicon surfaces by application of short laser pulses.

Figure 3:
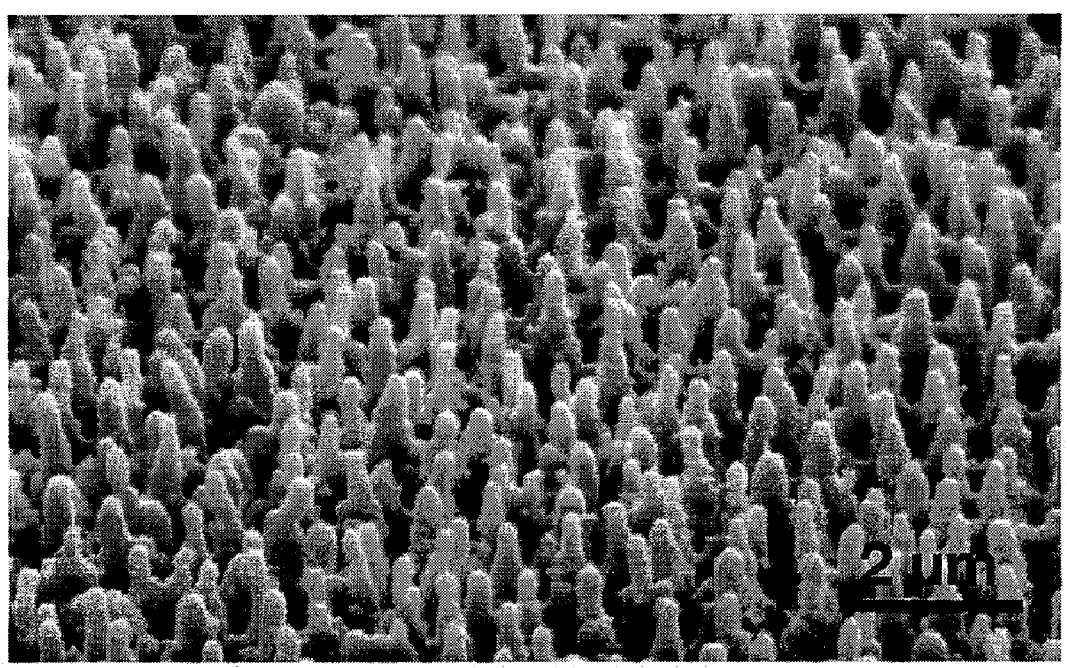
FIG. 3 shows nanosized structures, in the form of spikes, formed on a silicon surface by exposing the surface to a plurality of femtosecond pulses while the surface is in contact with water, FIG. 4A schematically depicts a top view of a metalized structured surface illustrating surface gaps that introduce discontinuities in the metal coating, which is characterized by a plurality of metalized regions and gaps between those regions, FIG. 4B schematically provides a perspective view of the metalized surface shown in FIG. 4A, illustrating the metalized regions, which are formed by a plurality of metal particles deposited on the structures of the surface, as well as gaps between different metalized regions, FIG. 5 schematically depicts a sensing substrate according to an embodiment of the invention in use for obtaining a SERS spectrum of an analyte, FIG. 6 schematically depicts the use of a sensing substrate according to an embodiment of the invention in observing a Raman "blinking effect,"

By way of illustration, FIG. 3 shows a silicon surface on which a plurality of nanosized features are generated via irradiation of the surface with a plurality of femtosecond laser pulses while the surface was in contact with water.

Figure 4A:
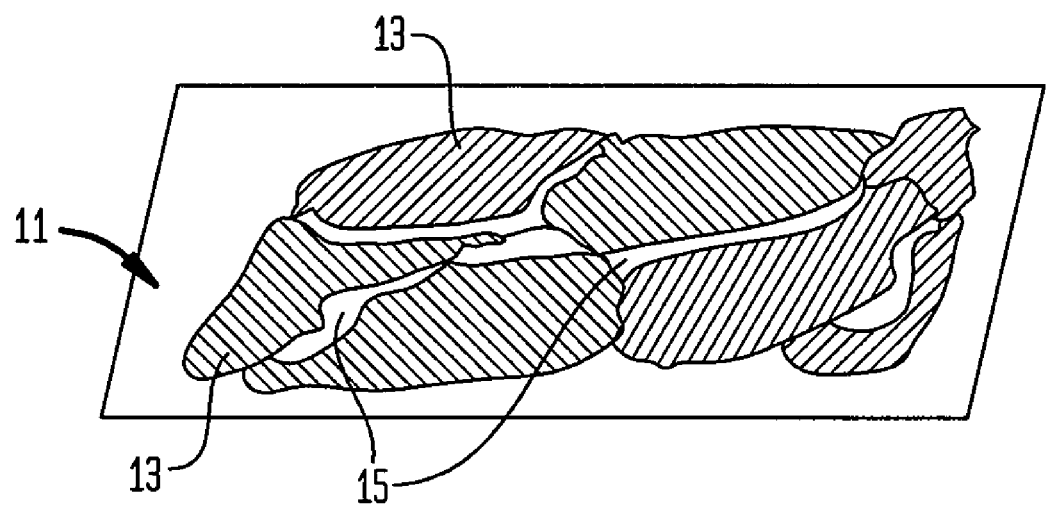
Figure 4B:
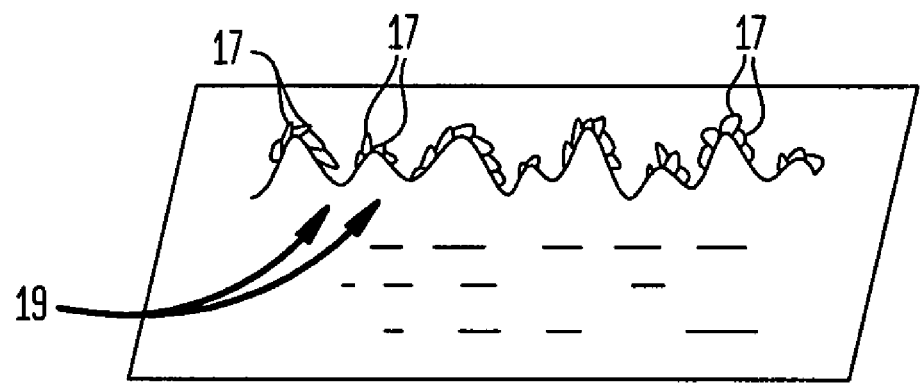

Referring again to the flow chart 10 of FIG. 1, in step (B), the structured semiconductor surface can be metalized, e.g., by deposition of silver or gold thereon, to generate a substrate for use in surface enhanced Raman spectroscopy (SERS), or other applications. As shown schematically in FIG. 4A (and discussed further below in the Examples section), the metalization of a structured surface 11 preferably results in coverage of a large portion of the structured surface with one or more metalized regions 13, e.g. in the form of aggregates of metal particles, with a plurality of the surface portions 15 (gaps between the metalized regions) remaining unmetalized. In other words, rather than having a uniformly thick metal coating that covers the entire surface, the metalized surface is characterized, as shown schematically in FIG. 4B, by aggregates of metal particles 17 that are deposited on the structured surface (e.g., on the tips and sides of the micron-sized or submicron-sized structures protruding above the surface as well as on troughs between the peaks) as well as a plurality of surface gaps 19 that are substantially devoid of the metal particles. Such surface gaps are typically formed on the sides of the protruding structures and on the surface regions between those structures. In many embodiments, these surface gaps, which can be formed without using a mask, generally have submicron-sized lateral dimensions, e.g., an average lateral dimension of the gap can be of the order of tens of nanometers.

In many embodiments, the metal particles forming the metalized coating regions can have average sizes less than about 1 micron, or less than about 500 nm, or less than about 100 nm. Without being limited to any particular theory, the micron-sized and/or submicron-sized surface structures (e.g., protruding cone-like features), which can be formed, e.g., by exposure of the surface to short laser pulses, can reduce the surface energy between the deposited metal and the underlying surface. This can in turn lead to the nucleation and growth of particles on the structured features, e.g., on their sidewalls, as opposed to formation of a smooth continuous metal film. In many embodiments, the metal particles can be separated from other particles by nanoscale gaps.

In many embodiments, the amount of metal deposited on the structured surface is controlled so as to form such surface gaps in the metal coating, e.g., to generate a non-uniform coating punctuated by non-metalized portions. By way of example, in some cases, the quantity of the deposited metal on the structured surface can correspond to a quantity that would produce a uniform metal coating on a putative smooth surface having the same macroscopic dimensions as that of the structured surface (a surface lacking the aforementioned micron-sized or submicron-sized features) with a thickness in a range of about 50 nm to about 500 nm, or in a range of about 50 nm to about 200 nm, or in a range of about 50 nm to about 80 nm.

A variety of metals and metalization techniques can be employed to form the discontinuous metal coating on the structured surface. Some examples of suitable metals include, without limitation, Au, Ag, Pt, Rh, Cu. Some examples of suitable metalization techniques include, without limitation, evaporation, sputtering, electroplating or other suitable metal deposition methods.

In some cases, the discontinuous metal coating generated on a structured substrate surface (e.g., structured silicon surface) can be characterized by its lower electrical conductivity relative to that exhibited by a substantially flat coating of that metal on a smooth surface of the substrate having the same macroscopic dimensions as that of the structured surface (e.g., smooth silicon surface) with a thickness corresponding to the deposition of the same quantity of metal as that deposited on the structured surface. For example, the DC electrical conductivity of the discontinuous metal coating can be at least about 50 times less than that of a respective continuous metal coating.

In some cases in which the underlying substrate is a doped semiconductor (e.g., silicon), the process of forming the structured features can result in the formation of an electrically insulating coating layer (e.g., an $SiO_2$ layer) over the structured surface. The discontinuous metalized coating layer is then formed over this insulating layer.

Figure 5:
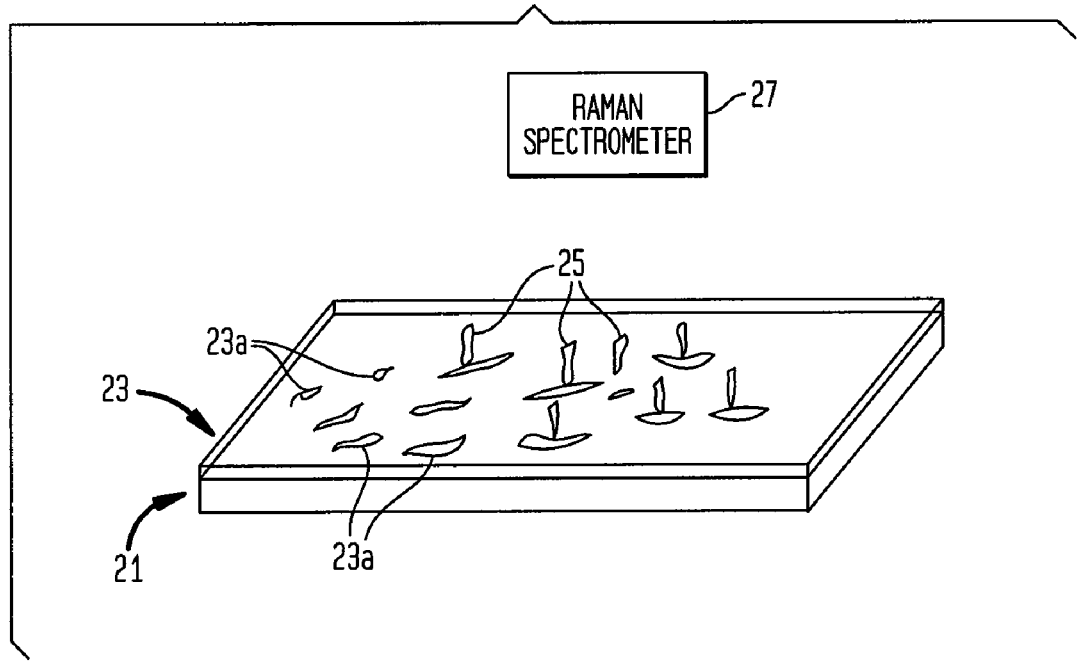

A metalized substrate of the invention can be utilized in a variety of analytical and/or diagnostic applications, such as Raman spectroscopy. By way of example, the metalized substrate can be utilized as a sensing substrate for performing SERS. For example, as shown schematically in FIG. 5, the sensing substrate can include a semiconductor wafer 21 having a structured surface on which a discontinuous metal coating 23 characterized by a plurality of gaps 23a is disposed (although the metalized regions of the coating are shown as substantially uniform for ease of illustration, in many embodiments, these regions are formed as aggregates of metal particles and can hence exhibit non-uniform topography). An analyte of interest 25 can be disposed over the surface, or in proximity thereof, and its Raman spectrum can be obtained by utilizing a Raman spectrometer 27. As discussed further below, in many cases, the Raman-active molecules deposited on the surface in the vicinity of the gaps in the metal coating are responsible for the bulk of the Raman enhancement achieved by utilizing the sensing substrate. In other cases, the substrate surface can be placed within an environment so as to be in contact with, or in proximity of, one or more molecular species in that environment. The Raman spectra of those species can then be measured so as to obtain information about the environment, such as the presense and/or quantity of one or more molecular species.

In many embodiments, the metalized substrates can provide a SERS enhancement factor greater than about $10^6$, or greater that about $10^7$, or greater than about $10^8$, preferably greater than about $10^9$, and preferably about $10^{10}$. Such enhancement factors can be measured, e.g., via protocols discussed in the examples that follow. Without being limited to any particular theory, in many embodiments, such SERS enhancement factors can be the result of optical resonances in metal nanoparticles deposited on the structured, e.g., laser-structured, substrate surface. Further, in many cases, a fraction of the Raman-active molecules deposited on the substrate surface at, or in proximity of, regions of large SERS enhancement provide a large portion of the Raman signal. In many embodiments, such regions of large SERS enhancement can be in proximity of surface gaps, e.g., nanosized surface gaps, between the metal particles deposited on the structured surface.

Figure 6:
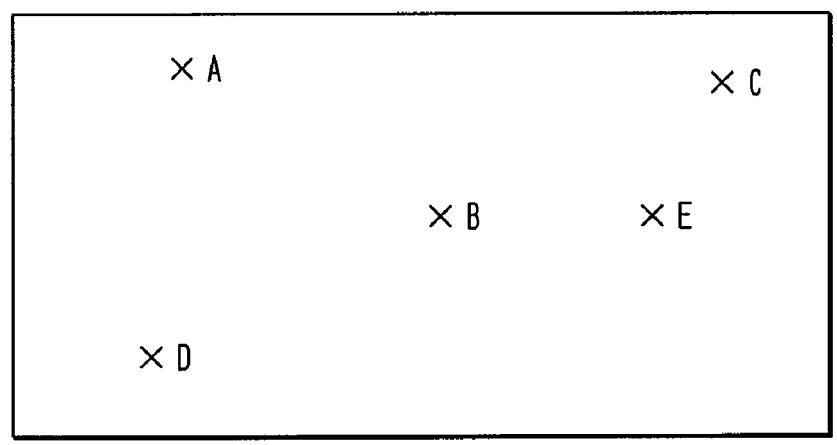
Figure 7:
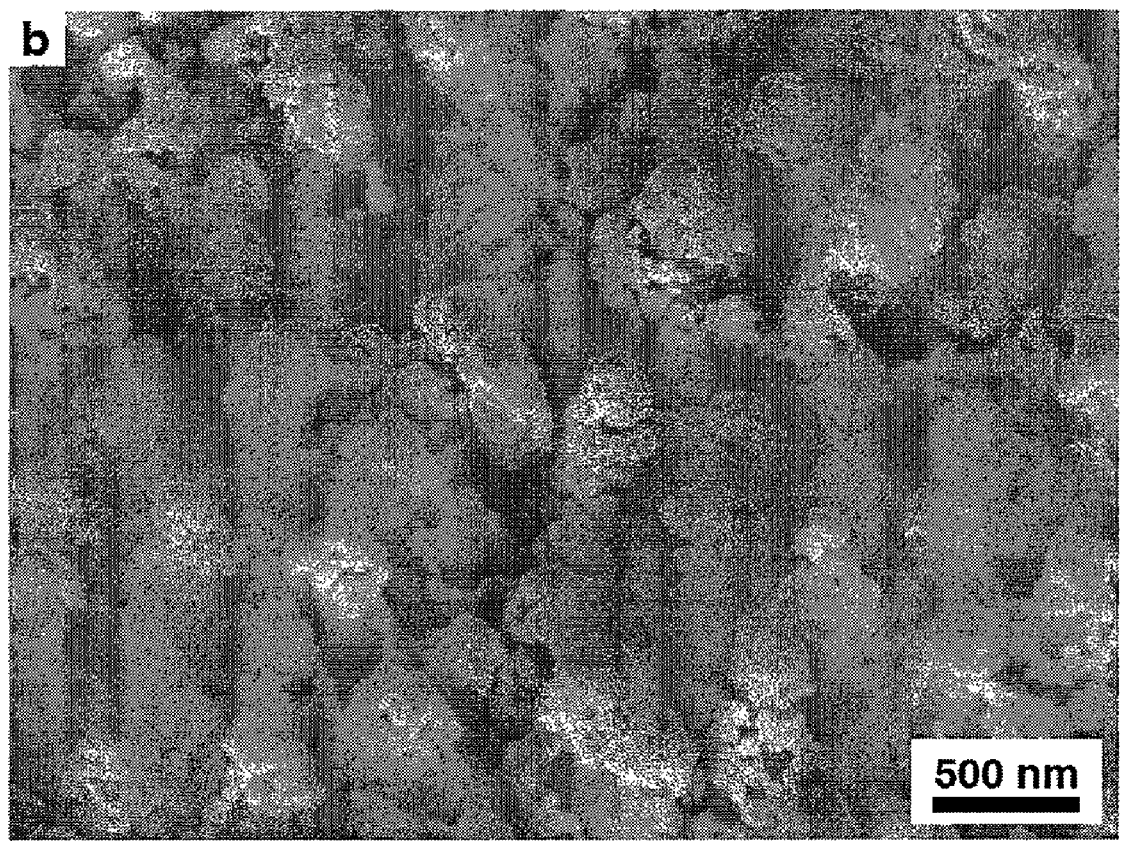
FIG. 7 is a scanning electron micrograph of a silver coated structured silicon surface according to an embodiment of the invention, illustrating a discontinuous metal coating characterized by a plurality of metalized regions and gaps between those regions.

In many cases, SERS enhancement provided by the metalized substrates of the invention is sufficiently large that a "blinking effect" can be observed even when a small quantity of Raman-active molecules, e.g., 10 molecules per 1×1 $micron^2$ macroscopic area (without considering surface enhancement due to surface structures) of the substrate surface, having normal (i.e. unenhanced) Raman scattering cross-sections in a range of about $10^{-29}$ $cm^2$ to about $10^{-31}$ $cm^2$ are disposed on the surface. For example, with reference to FIG. 6, spatially-resolved Raman signals from the surface would indicate intermittent Raman signals emanating from certain locations (e.g., locations A, B, C, D and E) at the surface. Such signals appear as a result of the thermally induced motion of the molecules. More specifically, the diffusion of a molecule into a high enhancement region (e.g., a region in proximity of a nanosized surface gap) can give rise to a Raman signal emanating from that region.

The applications of the sensing substrates of the invention are not limited to those discussed above. For example, the metalized substrates of the invention can find a variety of uses in areas that require intense optical fields at a surface.

Although in the above embodiments, the surface structures were formed by exposure of a substrate surface to short laser pulses, in other embodiments, the surface structures can be formed by employing other techniques, such as lithography.

The following examples provide further illustration of the salient aspects of the invention, and is provided only for illustrative purposes and to show the efficacy of the methods and systems according to the invention for significantly enhancing the signal-to-noise ratio in SERS. The examples, however, do not necessarily show the optimal results (e.g., optimal signal-to-noise ratios) that can be obtained by employing the substrates of the invention.

EXAMPLES

To fabricate SERS substrates, highly n-doped silicon (100) wafers were employed. A surface of each wafer was structured by exposing it to femtosecond (fs) laser pulses in a femtosecond laser surface structuring process discussed below. More specifically, a regeneratively amplified Ti:sapphire laser was used to generate 100 fs pulses with a center wavelength of 800 nm at a repetition rate of 1 kHz. The pulse train was frequency doubled to a center wavelength of 400 nm using a thin $BiBO_3$ crystal such that the second harmonic pulse width exiting the crystal was less than 200 fs. A highly n-doped silicon (100) wafer ($\rho$ (resistivity)=0.005-0.020 $\Omega \cdot cm$) was fastened inside a 10 mm deep cuvette, which was filled with deionized water. The laser pulses were loosely focused with a single lens to achieve an average fluence of 10 $kJ/cm^2$ at the sample. The cuvette was mounted on a two-axis translation stage, which translated the sample back and forth. The sample was translated at a speed such that each area of the silicon surface was subjected to approximately 500 pulses.

Figure 8:
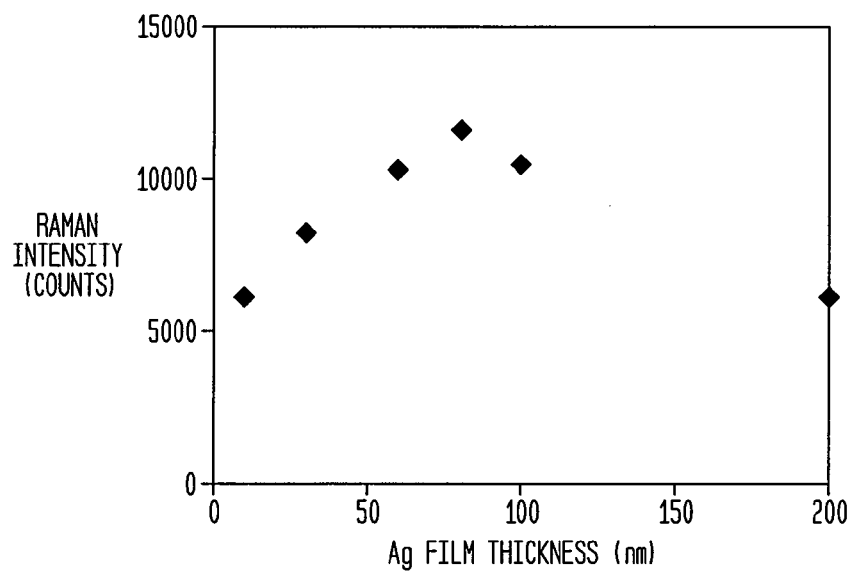
FIG. 8 shows a measured average relative intensity of the 1572 cm$^{-1}$ band (obtained at an excitation wavelength of 632.8 nm) of BTh SAM deposited on a structured silicon surface metalized with various quantities of silver in accordance with the teachings of the invention.

Subsequent to the laser structuring of the silicon surface, silver was thermally evaporated onto the structured surface. More specifically, an evaporator marketed by Sharon Vacuum Co, Inc. of Brockton Mass., U.S.A. under tradename The Sharon was employed to thermally evaporate silver onto the structured surface. By way of example, an evaporation rate of about 1.5 Angstroms/second, for a duration of about 8.75 minutes was employed to provide a coating having a nominal thickness of about 800 angstroms (as noted above, in many cases, the thickness of the coating is neither continuous nor uniform and the value of thickness simply refers to a nominal value). FIG. 8 shows a scanning electron micrograph of such a silver coated structured silicon surface, illustrating that silver particles cover the structures generated by laser exposure with nanosized gaps present between the silver coated surface portions. The quantity of silver deposited on the structured surface in this example corresponds to an 80 nm nominal thickness.

In order to estimate a SERS enhancement factor, a known quantity of molecules was deposited on the metalized structured surface before performing Raman spectroscopy on the substrates. To accomplish this, a self-assembled monolayer (SAM) of benzenethiol (BTh) or mecaptobenzoic acid (MBA) was applied to the substrates. In each case, a 4 mM solution of BTh or MBA was prepared with ethanol, and the SERS substrate (i.e., the substrate having metalized laser-structured surface) was submerged in the solution for 1 hour. The samples were then removed from the solution, gently washed in pure ethanol for 1 minute, and carefully blow-dried with dry nitrogen.

Raman spectroscopy was performed on the substrates using several different techniques. For example, a micro-Raman spectrometer using an s-polarized 5 mW, 632.8 nm HeNe laser, a 1200 gr/mm diffraction grating and deeply TE-cooled CCD array was used to collect Raman spectra and to estimate the SERS enhancement factor of the substrates. Using a 0.25 NA objective, Raman spectra were recorded from both a single spot on the substrate, and from a 500 micron (μm) thick cell of neat BTh, for normalization.

The same spectrometer was also used to characterize the dependence of the enhancement factor on the amount of silver deposited on the structured surface (this dependence is discussed further below in connection with FIG. 8). More specifically, several samples were fabricated with different quantities of deposited silver corresponding to following nominal silver thicknesses (that is, the thickness of a putative substantially uniform silver film that would be generated on a smooth surface (e.g., polished silicon surface prior to laser structuring) if that quantity of silver was deposited on that smooth surface): 10 nm, 30 nm, 60 nm, 100 nm, and 200 nm. After applying a SAM of BTh to each sample, Raman spectra were collected from ten different spatial points on each sample. The integrated intensity of the $1572 \pm 10\ cm^{-1}$ band from each point was averaged together to find the substrate (and consequently the amount of silver coating) that yielded the maximum SERS enhancement. FIG. 8 shows an averaged relative intensity of the $1572\ cm^{-1}$ band (obtained at an excitation wavelength of 632.8 nm) of a BTh SAM, covering substrates that are metalized with various quantities of silver (indicated in the graph as a nominal silver thickness). At this excitation wavelength, the substrate having a silver coating with a nominal thickness of about 80 nm yields the greatest average signal, which is about a factor of 2 larger than the average signals obtained from substrates having silver coatings with nominal thicknesses of 10 nm and 200 nm.

Figure 9:
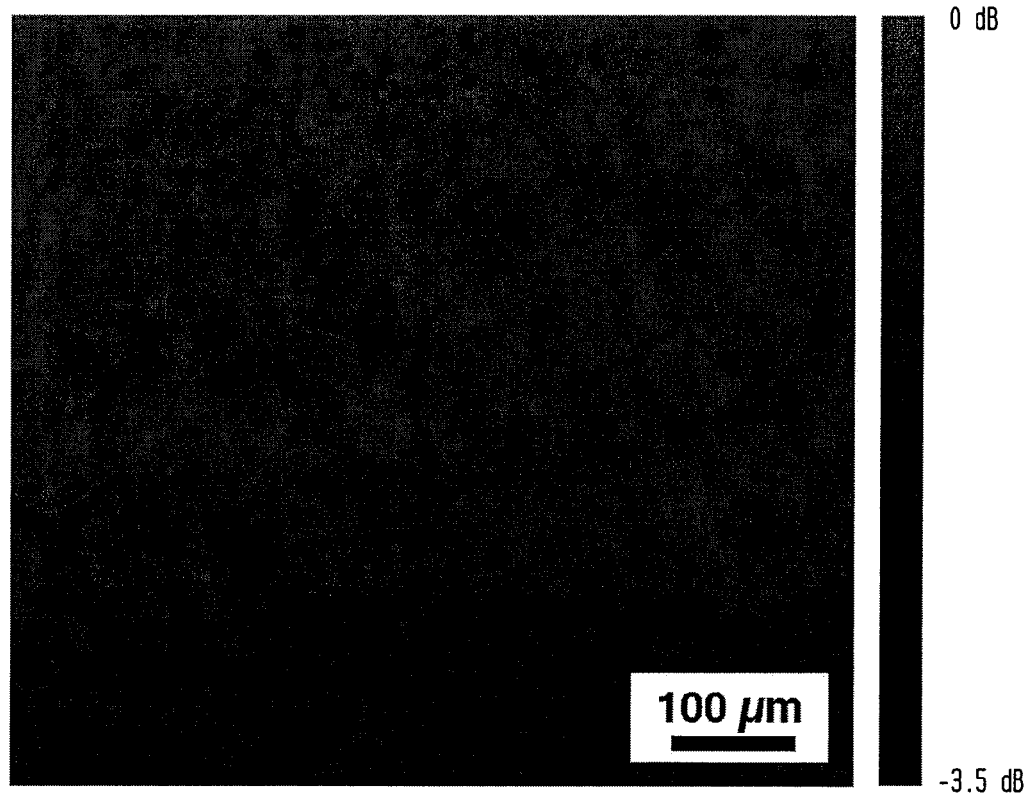
FIG. 9 is a Raman map collected from a silver coated (nominal thickness of 80 nm) structured silicon surface covered with BTh SAM.

To examine the spatial uniformity of the enhancement factor, a Raman map was collected from a silver coated (nominal thickness of 80 nm) structured silicon surface covered with BTh SAM, which is shown in FIG. 9. Using a 0.25 NA microscope objective, Raman spectra were recorded at 5 micron intervals, with an integration time of 0.5 seconds. An area of 0.5 mm by 0.6 mm was scanned; the map intensity was determined by the integrated intensity of the $1572 \pm 10\ cm^{-1}$ band. The Raman map shows the degree of uniformity of the Raman signal collected over a macroscopic (0.5 mm×0.6 mm) region of the substrate. The greatest deviation from the point of maximum signal is about 3.5 dB. The standard deviation of the intensity variation across the intensity map is about 13%.

The Raman scattering cross-section enhancement factor was calculated for the substrates by utilizing the following relation:

$$EF = (I_{SERS}/I_{Neat})(N_{Neat}/N_{SERS})$$

where, $I_{SERS}$ and $I_{Neat}$ are the integrated intensities of a specific Raman band, normalized to the incident laser photo flux, for a SERS substrate to which SAM is applied and for a neat sample, respectively. The enhancement is also normalized to the number of probed molecules in each sample, given by $N_{Neat}$ and $N_{SERS}$ for the neat and SAM substrates, respectively. The SAM density is taken at the highest reported value of ($6.8 \times 10^{14}$ cm$^{-2}$) for an unstructured silicon surface. $N_{Neat}$ was calculated using the molecular weight and density of neat BTh multiplied by the volume of the focused Gaussian HeNe laser beam.

Figure 10:
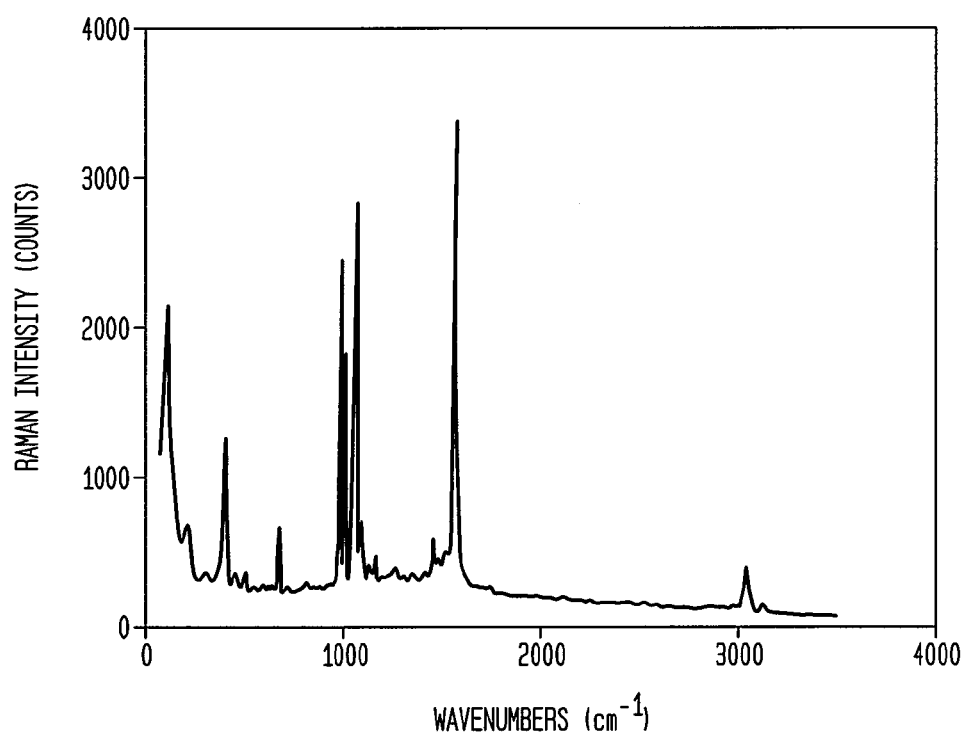
FIG. 10 is a Raman spectrum obtained from a BTh SAM disposed on a structured metalized silicon surface in accordance with an embodiment of the invention.

The SERS spectrum shown in FIG. 10 was obtained from a BTh SAM on a structured substrate surface with a 80 nm nominal silver coating (as noted above the silver coating is non-uniform and is punctuated with non-metalized surface portions). The SERS signal showed no discernable dependence on the sample orientation with respect to the excitation laser polarization. The absence of Raman peaks at 917 cm$^{-1}$ and 2567 cm$^{-1}$ due to S-H stretch and C-S-H bend modes indicates that a single monolayer of BTh has adsorbed on the surface. Using the calculated spotsize and densities for each sample, a preliminary SERS enhancement factor of approximately $2 \times 10^{11}$ was derived. However, the surface is not planar, and the effective BTh SAM density must be adjusted by a surface area enhancement factor, which takes into account the morphology of the substrates. The simplest model of the surface is to assume an array of appropriately sized silicon cones with an average period of ca. 500 nm. We model the surface as cones covered with a layer of spherical silver particles whose total cross-sectional area is equivalent to the surface area of the cones. This geometrical argument results in an additional surface area enhancement of approximately 10, which must be accounted for in the SERS enhancement calculations. Adjusting the preliminary SERS enhancement of $2 \times 10^{11}$ by the surface area enhancement factor of about 10 yields a SERS enhancement of about $2 \times 10^{10}$.

Figure 11A:
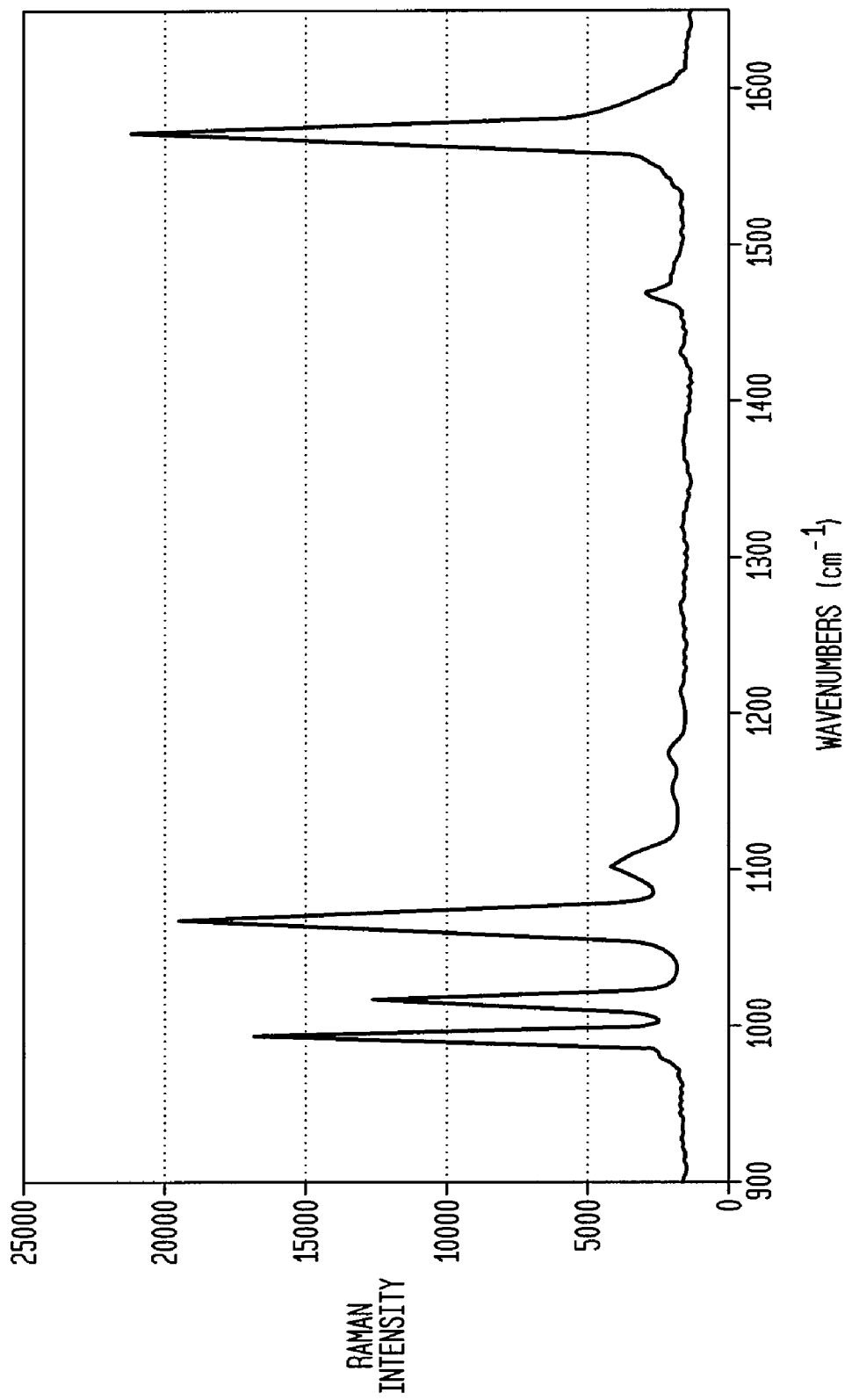
FIG. 11A presents the Stokes peaks of the 1572 cm$^{-1}$ band of a BTh SAM deposited on a silver coated structured silicon surface in accordance with one embodiment of the invention obtained with a 1 second integration.

By way of exemplary illustration, FIGS. 11A and 11B show, respectively, the Stokes and anti-Stokes peaks of the 1572 cm$^{-1}$ band of a BTh SAM deposited on a metalized structured silicon substrate surface with a nominal 80 µm silver coating. The spectra shown in FIGS. 11A and 11B were obtained with different integration times (1 second for the Stokes peaks and 100 second for the anti-Stokes peaks). As the signal scales linearly with time, a comparison between the Stokes and the anti-Stokes spectra can be obtained by normalizing the intensities based on the ratio of the integrations times (e.g., in this case dividing the anti-Stokes intensities by 100).

Figure 12:
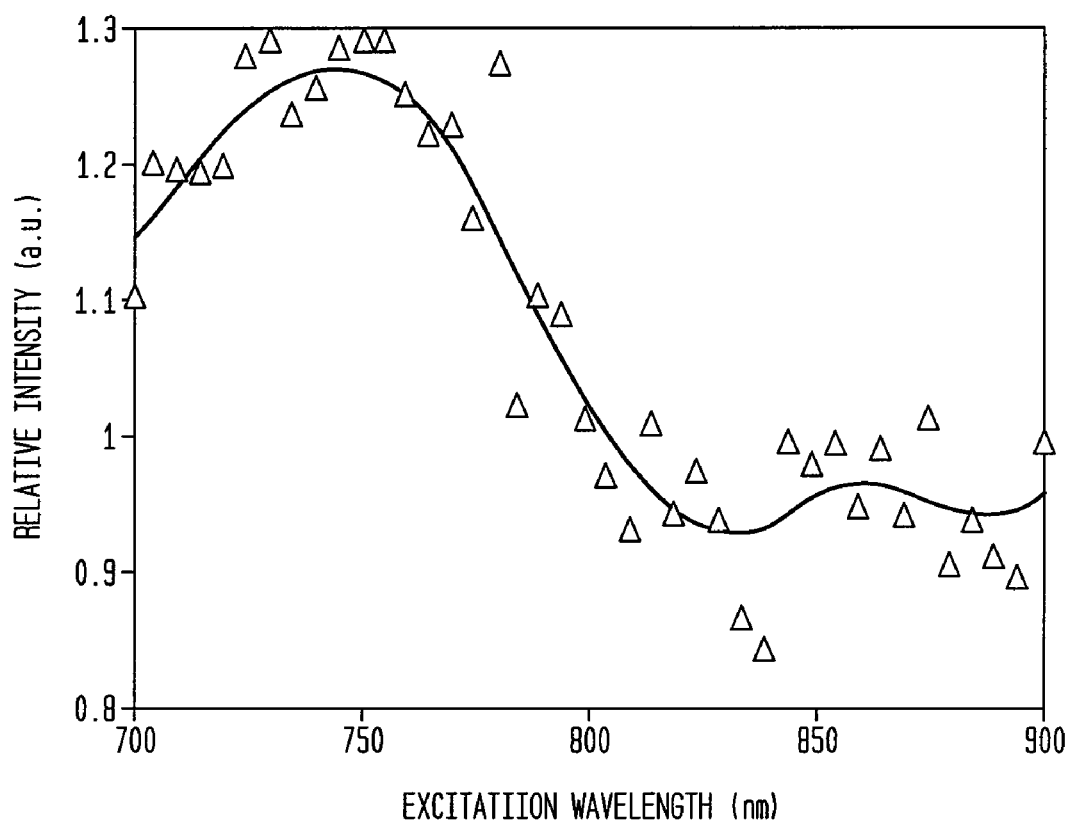
FIG. 12 is a non-resonant excitation profile of an MBA SAM disposed on a structured silicon surface metalized with silver.

A non-resonant excitation profile of an MBA SAM was used to determine the optimal excitation wavelength for the substrates. FIG. 12 shows the excitation profile of an MBA SAM covered structured silicon surface metalized with silver with a nominal thickness of about 80 nm. Examining the integrated intensity of the 1075 cm$^{-1}$ band, an optimal excitation wavelength can be discerned near 750 nm wavelength. As the Ti:Sapphire laser is tunable over a wavelength range of 700-900 nm, it is not certain that the observed excitation peak would correspond to a global maximum in enhancement. However, spectra of an MBA SAM taken with a Raman spectrometer at an excitation wavelength of 785 nm provided enhancement factors of approximately $10^9$. Comparing the excitation profile with the estimated enhancement factors at wavelengths of 785 nm and 632.8 nm indicates that the enhancement factor at 750 nm is likely to be very close to the enhancement factor at 632.8 nm. Even at 750 nm, the enhancement is only approximately 30% larger than the enhancement at 900 nm, showing that the substrate can operate efficiently over an extremely broad wavelength range.

It should be understood that the enhancement factor can be defined differently than that discussed above, which can lead to different numerical values for the enhancement factor. Regardless, the above exemplary data shows that a significant enhancement factor can be achieved by the use of the metalized structured sensing substrate. By way of example, an article entitled "Surface Enhanced Raman Scattering Enhancement Factors: A Comprehensive Study," authored by Le Ru et al. and published in J. Phys. Chem. C 2007, 111, 13794-13803 describes various definitions of SERS enhancement factors. This article in herein incorporated by reference in its entirety Those having ordinary skill in the art will appreciate that various modifications can be made to the above embodiments without departing from the scope of the invention.

What is claimed is:

1. A method of fabricating a sensing substrate, comprising
   exposing a substrate surface to a plurality of short laser pulses to generate a plurality of micron-sized and/or submicron-sized structures on said substrate surface to form a structured surface, and
   forming a discontinuous metal coating on said structured surface, wherein said discontinuous coating comprises a plurality of unmetalized surface regions.

2. The method of claim 1, wherein said coating comprises a plurality of metal particles.

3. The method of claim 2, wherein said metal particles have sizes in a range of about 50 nm to about 100 nm.

4. The method of claim 1, wherein the step of generating the micron-sized or submicron-sized structures comprises exposing the substrate surface to a plurality of short laser pulses.

5. The method of claim 1, wherein said substrate surface comprises a semiconductor surface.

6. The method of claim 1, further comprising placing said substrate surface in contact with a fluid while exposing it to said laser pulses.

7. The method of claim 6, wherein said fluid comprises a liquid.

8. The method of claim 1, wherein said step of forming a discontinuous coating comprises depositing a quantity of a metal on the structured surface and controlling said quantity of metal so as to generate a plurality of metalized coating regions separated by surface gaps of unmetalized regions on the structured surface.

9. A method of fabricating a sensing substrate, comprising
   exposing a semiconductor surface to a plurality of short laser pulses to generate a plurality of micron-sized or submicron-sized structures therein,
   depositing a quantity of a metal on said structured surface, and
   controlling said quantity of metal deposited on the structured surface so as to generate a plurality of metalized coating regions separated by surface gaps of unmetalized regions on said structured surface.

10. The method of claim 9, wherein at least one of said metalized coating regions is formed as an aggregate of a plurality of metal particles.

11. The method of claim 10, wherein said metal particles have a micron or a submicron average size.

12. The method of claim 9, wherein each of said metalized regions is separated from a neighboring metalized region by a nanosized surface gap.

13. The method of claim 9, wherein the step of depositing the metal comprises evaporating the metal onto the structured surface.

14. The method of claim 9, wherein said quantity of metal is selected such that its deposition on a hypothetical flat surface having substantially similar macroscopic dimensions as said structured surface would lead to a substantially uniform metal layer having a thickness in a range of about 50 nm to about 100 nm.

15. The method of claim 9, wherein said controlled quantity of the deposited metal corresponds to a quantity suitable for producing a uniform metal coating having a thickness in a range of about 50 nm to about 500 nm on a putative smooth surface having the same macroscopic dimensions as that of the structured surface but lacking said micron-sized or submicron-sized structures.

16. A diagnostic method, comprising generating a plurality of micron-sized and/or submicron-sized structures on a substrate surface by exposing the surface to a plurality of short laser pulses, depositing a quantity of metal onto said structured surface to generate a discontinuous metal coating characterized by a plurality of surface gaps distributed throughout said coating, and utilizing said metalized structured surface as a substrate for a diagnostic assay.

17. The method of claim 16, wherein said diagnostic assay comprises performing Raman spectroscopy.

18. The method of claim 16, further comprising controlling the quantity of the deposited metal to generate said discontinuous metal coating.

19. A sensing substrate, comprising a semiconductor substrate having a surface characterized by a plurality of micron-sized or submicron-sized structures formed by exposing the surface to a plurality of short laser pulses, a metalized coating disposed on said structured surface, said coating including one or more metalized regions and a plurality of unmetalized gaps, wherein one or more of said unmetalized gaps have submicron-sized lateral dimensions.

20. The sensing substrate of claim 19, wherein said metalized regions comprise a plurality of metal particles.

21. The sensing substrate of claim 20, wherein said particles have sizes less than about 1 micron.

22. The sensing substrate of claim 19, wherein said metalized coating exhibits a DC electrical conductivity that is at least about 50 times less than that of a substantially flat coating of the same metal on a putative smooth surface of said substrate having the same macroscopic dimensions as that of the structured surface with a thickness corresponding to the deposition of the same quantity of metal as that deposited on the structured surface.

* * * * *